(12) United States Patent
Yankielun et al.

(10) Patent No.: US 7,130,780 B2
(45) Date of Patent: Oct. 31, 2006

(54) METHOD AND INSTRUMENT FOR ELECTRONICALLY RECORDING AND IMAGING FLUID WASHOVER VIA MEASURING CHARACTERISTICS OF THE FLUID AT MULTIPLE LOCATIONS SIMULTANEOUSLY

(75) Inventors: Norbert E. Yankielun, Lebanon, NH (US); James H. Clark, Lyme, NH (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 742 days.

(21) Appl. No.: 10/318,297

(22) Filed: Dec. 13, 2002

(65) Prior Publication Data

US 2003/0117154 A1    Jun. 26, 2003

(51) Int. Cl.
*G06G 7/48* (2006.01)
*G01R 27/08* (2006.01)

(52) U.S. Cl. .............................. 703/6; 703/9; 324/691; 324/722

(58) Field of Classification Search ............... 703/6, 703/9; 324/691, 722
See application file for complete search history.

(56) References Cited

U.S. PATENT DOCUMENTS

| 2,217,843 | A | * | 10/1940 | Langer | 324/239 |
| 2,709,785 | A | * | 5/1955 | Fielden | 324/701 |
| 3,729,013 | A | * | 4/1973 | Anderson | 137/93 |
| 3,993,945 | A | * | 11/1976 | Warmoth et al. | 324/449 |
| 4,288,308 | A | * | 9/1981 | Hach | 204/420 |
| 4,480,323 | A | * | 10/1984 | Page | 367/131 |
| 4,650,458 | A | * | 3/1987 | Dahlberg et al. | 604/6.06 |
| 4,690,749 | A | * | 9/1987 | Van Alstine et al. | 204/454 |
| 5,503,026 | A | * | 4/1996 | Bohm et al. | 73/861.11 |
| 5,517,202 | A | * | 5/1996 | Patel et al. | 343/709 |
| 6,232,786 | B1 | * | 5/2001 | Barnett | 324/691 |
| 6,609,071 | B1 | * | 8/2003 | Shapiro et al. | 702/50 |
| 6,673,622 | B1 | * | 1/2004 | Jina | 436/69 |

OTHER PUBLICATIONS

A flow rate and conductivity transduxer for centrifuge-borne membrane process measurements; Meas. Sci. Tech. 11 (2000) 1440-1446.*

* cited by examiner

*Primary Examiner*—Hugh Jones
(74) *Attorney, Agent, or Firm*—Earl H. Baugher, Jr.

(57) ABSTRACT

An array of electrically isolated electrode pairs in combination with a specially configured processor, e.g., a personal computer, is employed to obtain a continuous real-time acquisition, processing, mapping and visualization of fluid washover. In a specific application, washover data are collected on salient electrical characteristics of seawater accumulating between electrodes of an electrode pair, one of which may be a common ground plane. For example, the resistance of seawater is measured dynamically at each electrode pair. These data are then processed using specialized software to yield representation of the dynamics of selected washover events on a surface of interest. Described systems specifically provide real-time spatial and temporal representations of interaction, including two and three-dimensional visualization of the washover, as well as recording selected data for future use. Methods of employment of the system are also described.

44 Claims, 17 Drawing Sheets

METHOD AND INSTRUMENT FOR ELECTRONICALLY RECORDING AND IMAGING FLUID WASHOVER VIA MEASURING CHARACTERISTICS OF THE FLUID AT MULTIPLE LOCATIONS SIMULTANEOUSLY

STATEMENT OF GOVERNMENT INTEREST

The invention described herein may be manufactured and used by or for the United States Government for governmental purposes without the payment of any royalties thereon.

FIELD OF THE INVENTION

The present invention relates generally to detection of parameters by electronic means and more particularly to the real time detecting, recording and representing visualization of the interaction of an object with its environment, and most particularly the interaction caused by a material, preferably a fluid, passing over an object.

BACKGROUND

It is important to know the three-dimensional (3D) spatial and temporal parameters of seawater washover of low-profile towed bodies, buoys, and other maritime towed, tethered and free-floating objects. Among other advantages, this knowledge assists in understanding and improving hydrostatic and hydrodynamic performance of a towed body in a wide variety of sea states.

Washover is defined as the condition of occasional (not "frequent," continuous or permanent) partial or complete inundation and exposure of a top surface of a floating object to a fluid. Typically, at sea washover is caused by wave action, wind action, the dynamics of towing the floating object (body) or a combination of the interaction of these factors. Washover may adversely affect performance of floating objects equipped with electronic devices such as antennas, photovoltaic arrays, instrumentation, radio, and auditory or visual beacons. For a low-profile towed body, washover depth is usually within the range of less than a centimeter (0.4") to 30 cm (12"). Typically, an inundation has a duration of less than one second.

The ability to capture key parameters of washover as data as well as to visualize washover events in real-time enables designers to improve hydrostatic and hydrodynamic profiles of these objects. Currently, there are no purpose-built devices, systems, or methods that provide this information. Thus, there exists a need for a Washover Electronic Measurement System (WEMS) for real-time acquisition, three-dimensional mapping, and visualization of seawater washover dynamics. The real-time data acquired with WEMS may be used to analyze hydrodynamics, electromagnetic interaction with seawater, and, in conjunction with computer simulations and modeling, to optimize hardware design.

A preferred embodiment of the present invention uses electronic techniques to provide a method and apparatus that facilitates real-time acquisition of pertinent parameters to enable two or three-dimensional mapping and visualization of washover. In a specific application, it provides an empirically based benchmarking process for computational fluid dynamic assessments of turbulent flow around arbitrarily shaped surface towed bodies.

SUMMARY

A system detects, measures and records fluid washover of an object, including displaying a representation thereof in real time. The "fluid" need not be a liquid. It only need show a measurable contrast between states where it is present and absent, and also possibly indicate the degree of presence volumetrically, such as depth of accumulation. Air flow, moist air, airborne dust, airborne anthrax, etc. do not have enough volumetric density (i.e., particles per cc) to be very different from ambient air, thus a typical sensor would not see the difference unless it were extremely sensitive, i.e., laboratory quality. Denser materials work better with a sensor having a reasonably designed sensitivity. For an electrical conductivity method, conductive (low resistivity or high loss) "fluids" are detected, e.g., blood, seawater, brine, etc. Conductive powders or granular materials, e.g., iron filings, iron oxide power, powdered carbon, or other conductive powder/granular materials would be detected also. For a capacitive approach, low-loss dielectric materials, be it liquid, granular, or powder, may be detected. These low-loss dielectrics include but are not limited to: sand, silt, gravel, powdered and granular plastic, flour, grain, oils, accumulating snow, ice, freshwater, etc.

In one embodiment, the preferred embodiment uses an array of electrically-isolated electrode pairs flush-mounted to the external side of a surface of interest of the object. The configuration of the array, i.e., spacing between electrode pairs and overall size, is chosen to provide a pre-specified level of detail needed for display. An electric potential is maintained between the electrodes of each electrode pair during operation of the system. An electrical connection between each electrode of the electrode pairs is provided to a data collection, processing, recording and display sub-system, e.g., a personal computer (PC) equipped with a monitor and a data collector/processor, such as a multi-channel multiplexed printed circuit board incorporating an analog-to-digital converter, and loaded with appropriately configurable software. The active electrode of the electrode pair is powered by a suitable source via a wire connection such as a shielded coaxial cable.

The sub-system collects data representing the sampling of at least one electrical characteristic of any fluid accumulating between the electrodes of each electrode pair, processing the data for real time display as well as recording selected data for future use. The electrical characteristic chosen for measurement may be any of the following: resistance, complex impedance, inductance, capacitance, and any combination thereof. One electrode in each pair is electrically activated and the other is held at an electrical potential common to all like said electrodes in the array of electrode pairs, e.g., for each electrode pair in the array, one electrode of the pair is grounded while the other is held at a pre-specified voltage. In this way each of the grounded electrodes may be connected to a common ground to simplify wiring. Grounding and shielding are done according to good electrical engineering practice to minimize cross-talk between sensors and minimize pickup of extraneous interfering electronic signals, e.g., interference from nearby radio transmissions, cell phones, etc.

The electrodes may be any of various types of machine screws inserted in counter-bored holes in the surface of interest so as to be flush-mounted in the external side of the surface. The electrodes may also be capacitive devices affixed to the internal side of the surface of interest or affixed to the external surface and covered with a thin coating of a dielectric, such as a polyurethane. The electrical connections between the electrodes and the sub-system may be wires incorporating an electrically insulating cover, such as a shielded coaxial cable. Each of these wires may be bundled with like wires to facilitate a durable connection to the sub-assembly.

A particular embodiment of the present invention envisions the fluid to be a liquid and the object floating in the liquid such that the liquid does not cover at least part of the object when the liquid is not acted on by external forces. A specific embodiment would display seawater washover of a towed body.

Also provided is a method for using a preferred embodiment of the present invention. The method for detecting, measuring and recording fluid washover of an object includes displaying a representation of fluid washover in real time. It is accomplished by providing an array of electrically-isolated electrode pairs that are affixed to a surface of interest. In one embodiment they may be flush-mounted to the external side of a surface of interest of said object. In another embodiment, capacitive electrodes may be affixed to an internal side of the surface of interest. By maintaining an electric potential between the electrodes of each electrode pair, certain electrical characteristics are collected as data during selected washover events. These characteristics are selected to vary based on the amount and timing of fluid accumulating between each electrode pair. These data are processed and selected data are either displayed in real time, recorded for later use, or both. This method enables visualization of selected washover events via a real time display as well as recording selected representations of washover events for future use. Electrical characteristics that may be measured include: resistance, complex impedance, inductance, capacitance, and any combination thereof.

The method involves electrically activating one electrode in each electrode pair while the other electrode is held at an electrical potential common to all like electrodes in the array of electrode pairs. In a preferred embodiment, the electrodes held at a common potential are maintained at ground. In a preferred embodiment, this method is used to determine washover of a liquid with the object floating therein such that at least part of the object is covered with the liquid when the liquid is not acted on by external forces. In a specific application, the object is a towed body that may be washed over by seawater.

Further, a preferred embodiment of the present invention may be implemented in a simulator such that an expensive object of interest is simulated by a model that mimics its shape, center of gravity, mass, orientation, etc. The model may be provided as a full-scale or partial scale replica of the object with the configuration of the electrode array scaled accordingly.

Implementation of a preferred embodiment of the present invention provides continuous real-time acquisition, processing, mapping and visualization of washover events for military, industrial, and commercial users. It uses an electrode array to provide continuous, real-time mapping and visualization of washover. It specifically provides real-time spatial and temporal visualization of washover, including two and three-dimensional visualization of washover. Some applications include:

provides a tool for hydrodynamic and hydrostatic evaluation of a body subjected to washover;
provides a tool for electromagnetic, auditory, and visual performance evaluation of a body subjected to washover; and
enables objective real time evaluation of towed body washover, hull hydrodynamic performance, buoy and tethered body hydrodynamics, and vessel superstructure washover.

There are several general advantages to the implementation of a preferred embodiment of the present invention in any of the above applications:
simple to implement;
inexpensive to implement, operate, and maintain;
collects washover data in real-time;
requires minimal training of system installers, operators, and maintenance personnel;
adaptable to various shapes; and
provides visualization in both real-time and after processing collected data.

DETAILED DESCRIPTION

In a preferred embodiment of the present invention, systems and methods for measuring interaction of an object with its environment, e.g., washover thickness of seawater or "washover mapping," are provided. A method of a preferred embodiment is based on taking resistivity readings. Further, other electrical parameters, including capacitance, inductance and complex impedance may be taken to yield washover mapping. Measuring resistance is most effective in a conductive (low resistivity) media, such as seawater. The other measures may be more appropriate for taking washover data in more highly resistive media, such as fresh water. As known to one skilled in the art, implementation of systems that exploit capacitance, inductance and complex impedance is a minor extension, or modification, of the techniques discussed below To obtain an indication of washover thickness based on resistivity, a first order approximation equation has been developed from examination of the Wenner earth resistivity method commonly used in geophysical profiling and mapping of ground stratigraphy. Parasnis, D. S., *Principles of Applied Geophysics,* Chapman and Hall Publishers, New York, 1986.

Figure 1:
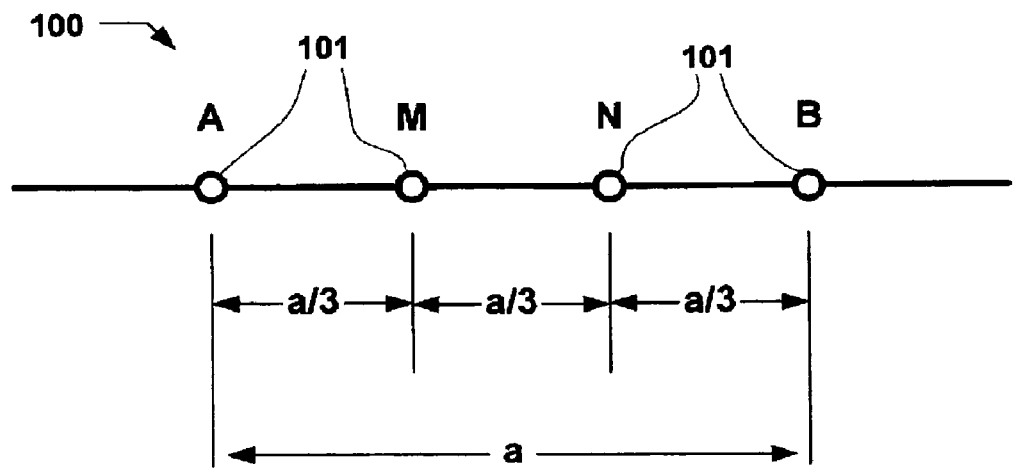
FIG. 1 is a schematic of the relative spacing of electrodes using the Wenner resistivity measurement method.

Refer to FIG. 1. The Wenner resistivity measurement 100 employs a four-electrode method. Electrodes 101 are indicated as A, M, N, and B. Electrodes A and B are potential (voltage) probes while M and N are current injection electrodes. These electrodes are spaced in a line at a distance, a/3, one from another, for a total included length of a. As a "rule of thumb", the maximum discernable depth, $d_{max}$, of electric field penetration as related to the sensor configuration 100 of FIG. 1 is:

$$d_{max} = \left(\frac{2}{3}\right)\left(\frac{a}{3}\right) = \frac{2a}{9} \tag{1}$$

For $d_{max}$, the resistance, R, of a cylindrical volume of length, a, and a radius of a/9, i.e., a cylinder long in relation to its diameter, where a is given in centimeters (cm), is:

$$R = \frac{\rho a}{\pi \left(\frac{a}{9}\right)^2} \tag{2}$$

where:

R=resistance in ohms (Ω)

and

ρ=resistivity in ohm-centimeters (Ω-cm).

Figure 2:
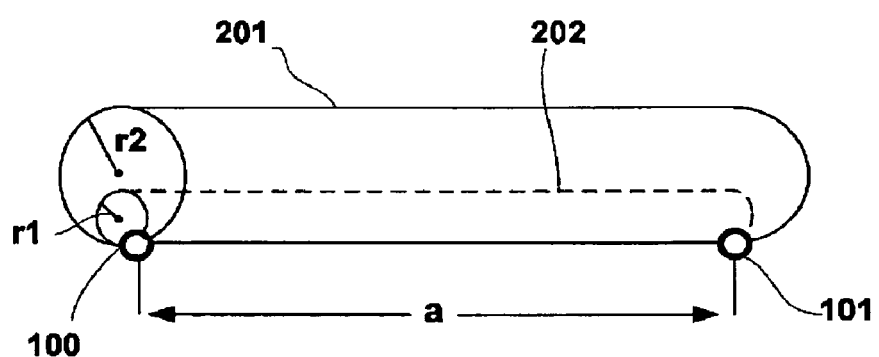
FIG. 2 is a schematic showing relative thickness of washover between electrodes as cylinders of differing radius.

Refer to FIG. 2. Applying this geophysical concept to seawater washover measurements and considering washover to be a cylinder, where the thickness of washover, i.e., diameter of the cylinder, will vary from zero to several centimeters or more, Eqn. (2) is modified to accommodate this variation in washover thickness. Substituting an arbitrary radius, r (cm), (0<r≦$d_{max}$), the resistance, R, of a cylindrical volume 201, 202 of seawater (as a function of r) is given by:

$$R = \frac{\rho a}{\pi r^2} \tag{3}$$

where 2r is the thickness of washover. Thus, for purposes of "imaging" or "visualizing" washover, 2r, is obtained by re-writing Eqn. (3) as $$2r = 2\left(\frac{\rho a}{\pi R}\right)^{\frac{1}{2}} \tag{4}$$

and measuring R via electrodes spaced apart at a distance, a. This distance, a, is chosen to permit a pre-specified level of detail in the subsequent display of the representation of washover. In one example, electrical resistance provided by any fluid, such as seawater, present between the electrodes 401, 402 (shown as possible variations in FIG. 4) completes the circuit between the active electrode 401 and its paired ground electrode 402, thus enabling measuring an electrical characteristic of the seawater "cylinder," e.g., a measure of resistance, R, for use in Eqn. (4). Each of these measures is then converted by configurable software to yield a "dynamic" image of the washover over the entire configuration 500 in real time.

EXAMPLE I

Figure 3:
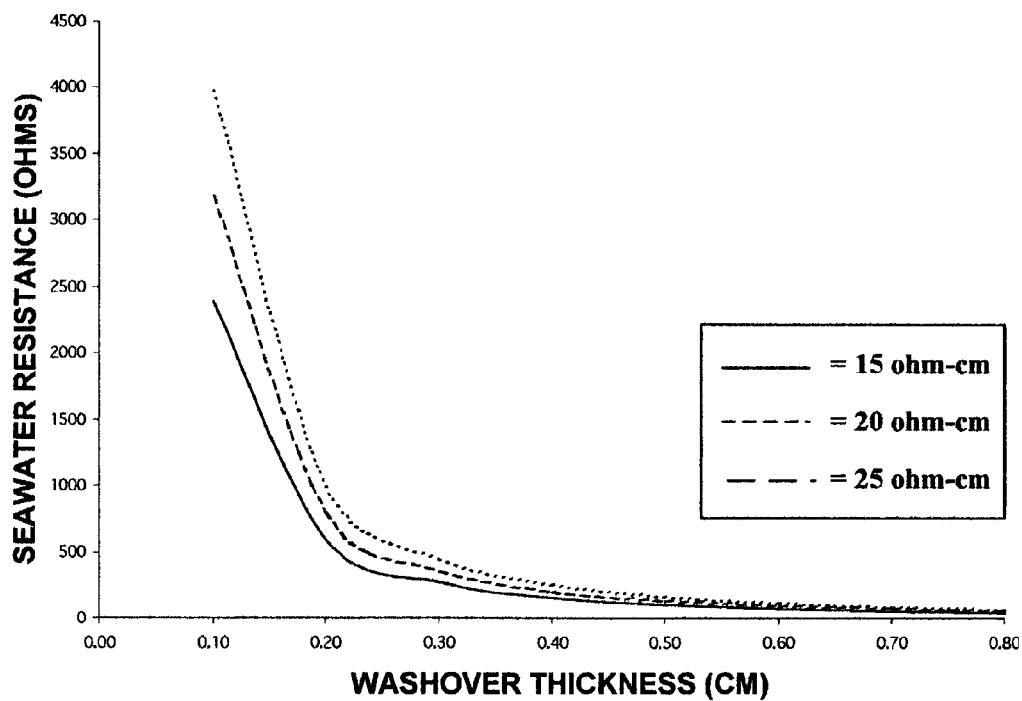
FIG. 3 is a graph of the relationship between the resistance of seawater and washover thickness for three values of seawater resistivity, $\rho$.

Refer to FIG. 3 depicting the relationship of resistance to washover thickness for three values of seawater resistivity, ρ, at 15, 20, and 25 Ω-cm. (Seawater resistivity has a normal range of 15–25 Ω-cm, or stated another way, a conductivity, σ, of 6.7–4 Siemens (S)). As is evident from FIG. 3, resistance of a given amount of the seawater varies little for washover thickness greater than 0.2 cm. Thus, for a given volume of wash over seawater, seawater resistance does not vary with depth of washover. Thus, any resistance measures taken from the "cylinder" of seawater present in washover between any pair of electrodes 401, 402 will be independent of the relative thickness of the washover and be representative of the actual thickness of washover at that point and at that time.

Using Eqn. (1), for an inter-electrode spacing of active electrodes, a, of 3.6 cm and a seawater washover thickness 2r of 0.1–1.0 cm, $d_{max}$, is calculated to be 0.798 cm (0.3"). While electric field penetration continues even to greater depth than this "rule of thumb" suggests, at $d_{max}$ there is very little change in resistance of a given volume in the seawater "cylinder" as the unit depth (2r) increases. Thus, over a limited range of interest, seawater washover thickness may be approximated directly as a function of measured resistance, e.g., the thinner the thickness (cylinder) of washover, the more the resistance will be. Note that it makes no appreciable difference whether the seawater cylinder is large or small as to the approximate resistance of a given amount of seawater within either the large or small cylinder. While this method is a first order approximation, the process may be defined in a more mathematically rigorous manner, established experimentally, or both.

Figure 4:
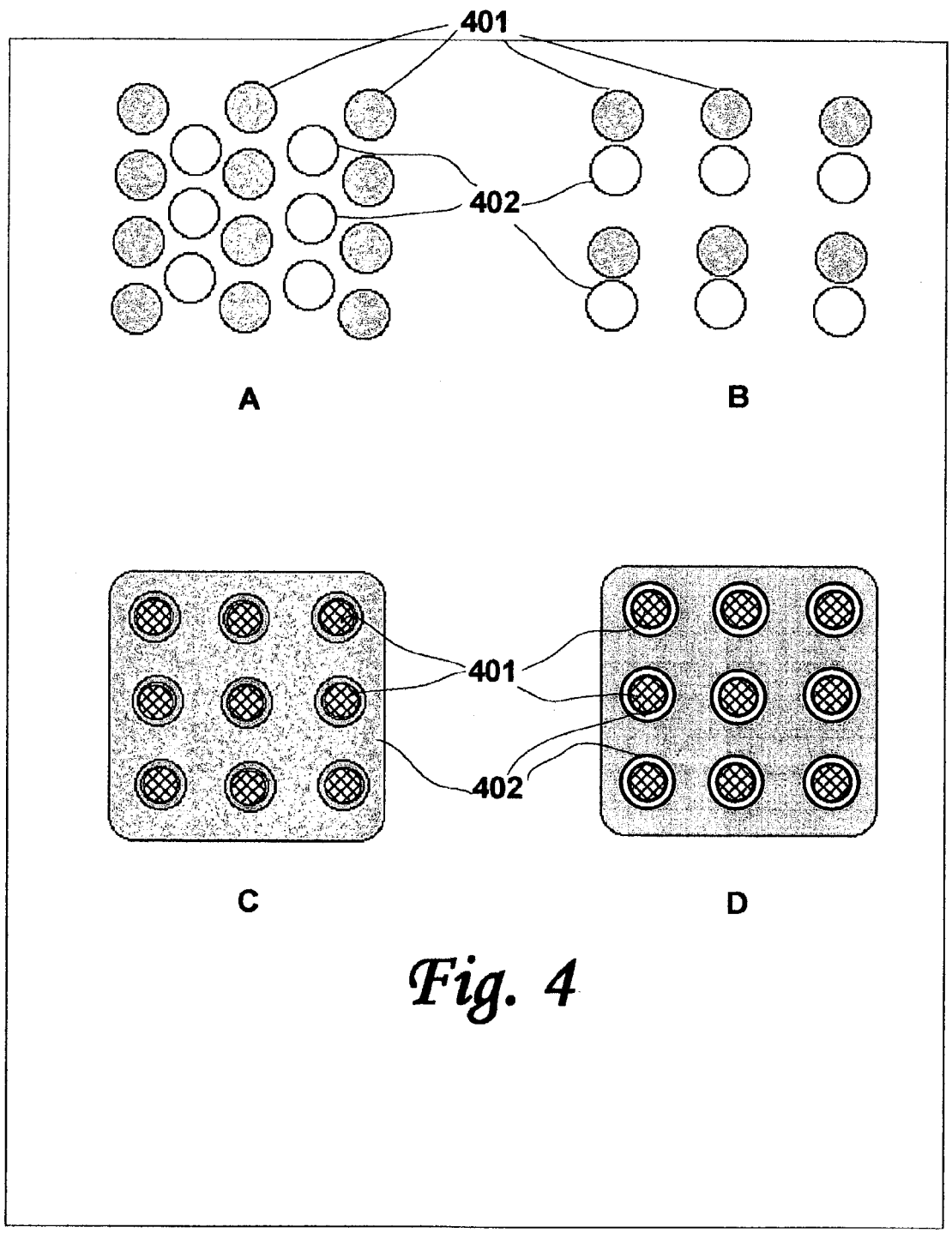
FIG. 4 depicts four configurations for electrodes that may be used in a preferred embodiment of the present invention.

Refer to FIG. 4. For FIG. 4 and subsequent figures, shaded portions represent an active electrode while enclosed white (unshaded) portions of electrodes represent electrical ground. A configuration employed in a preferred embodiment may comprise a two-dimensional array of electrode pairs arranged in any of a number of uniform matrices over the region of interest (normally a top side) of the test object. For example, FIG. 4A depicts a "clustered" array of electrode pairs 401, 402 while FIG. 4B depicts a "paired" array. FIG. 4C depicts a ground plane 402 with a series of electrically isolated (active) electrodes 401 in an array and FIG. 4D represents an array of electrode pairs 401, 402 coaxially arranged and embedded in an electrically insulated substrate, i.e., the center is the active conductor 401, and the ground conductor 402 is electrically separated from and surrounds the active central electrode.

Figure 5:
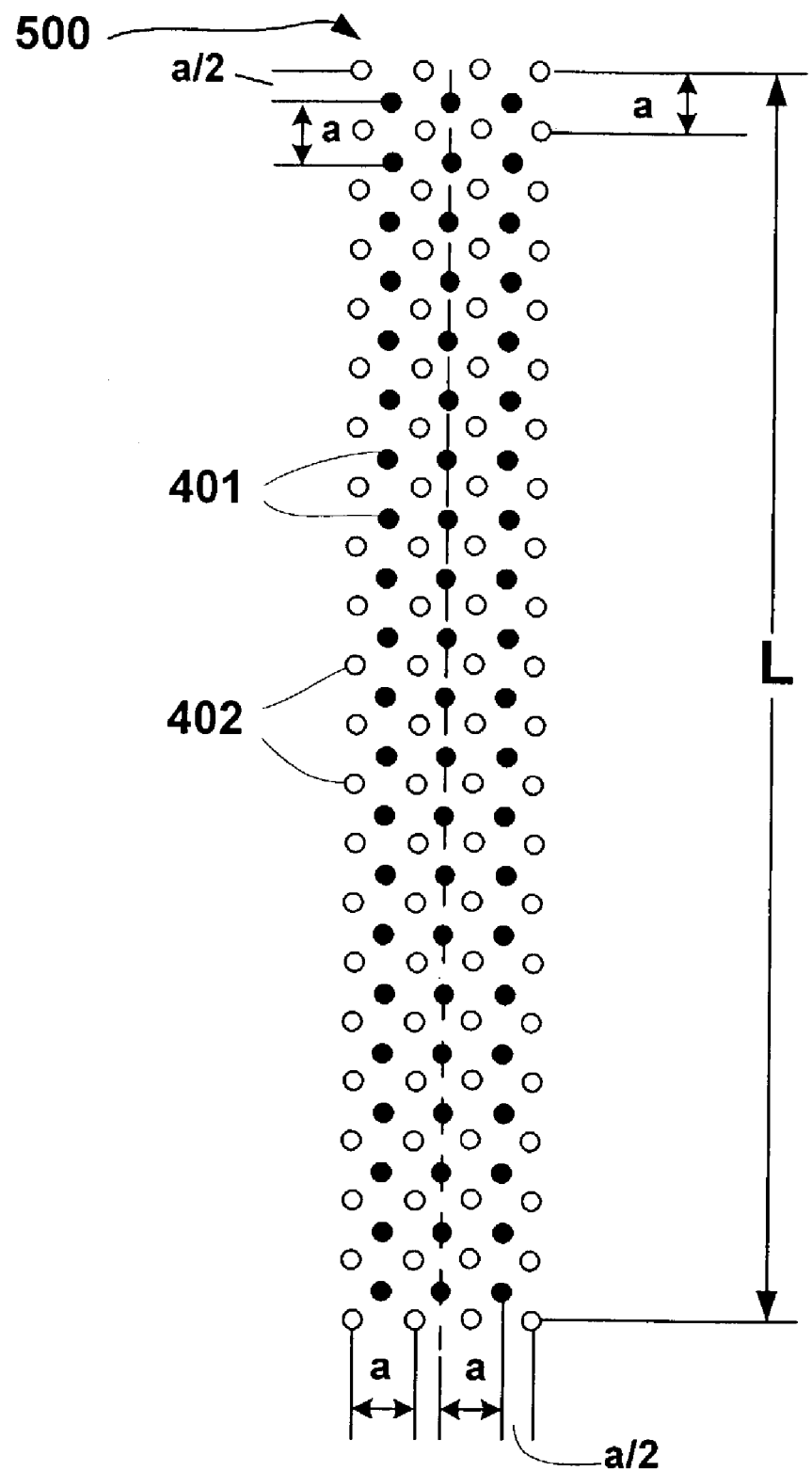
FIG. 5 depicts a 3×21 array of active electrodes that may be used with a preferred embodiment of the present invention.
Figure 9:
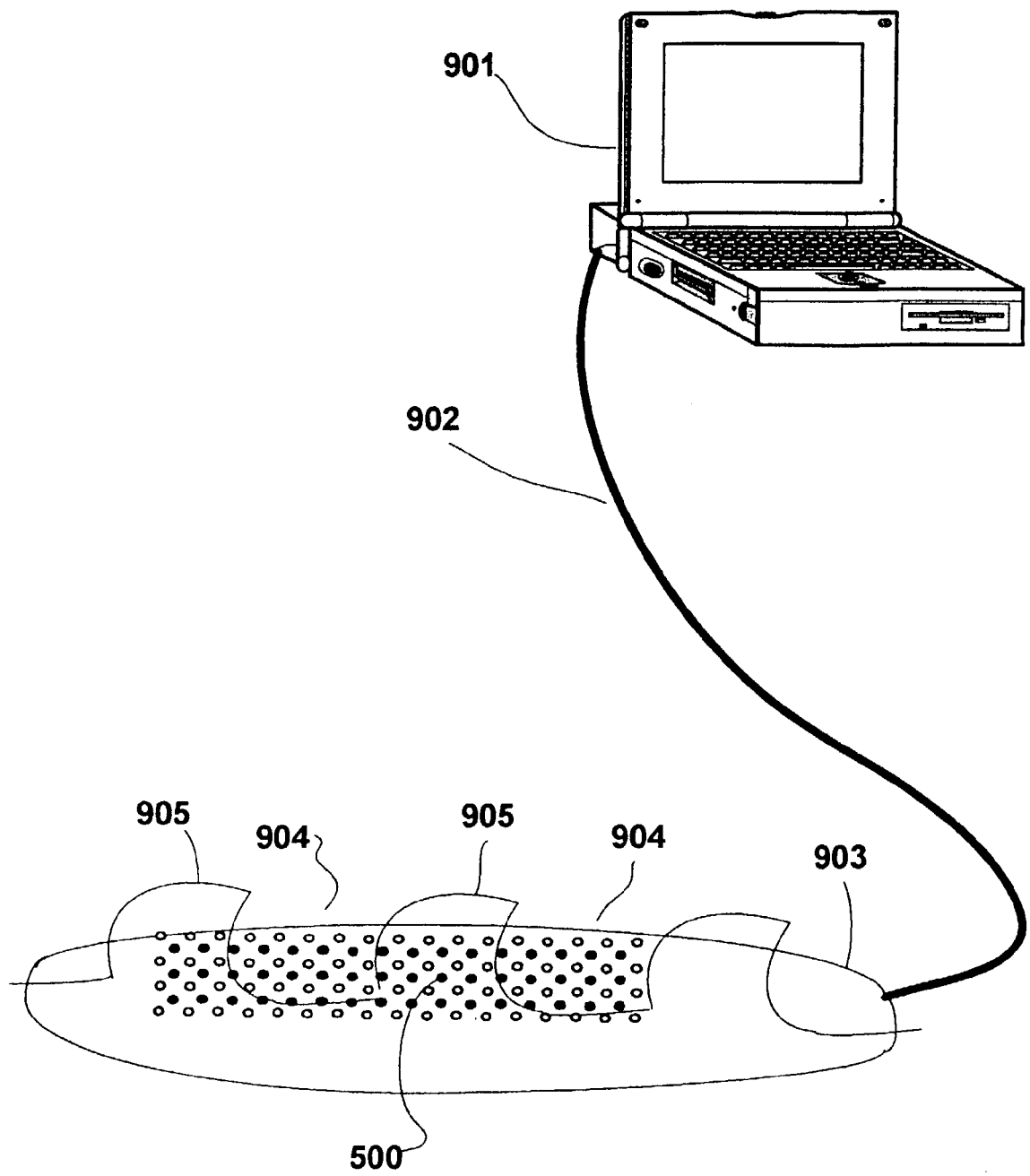
FIG. 9 depicts a preferred configuration for taking data characterizing washover from an object experiencing washover.

Refer to FIG. 5 in which a 3×21 matrix 500 of active electrodes 401 of overall length L is shown. Surrounding each of the active electrodes 401 in the array are four "common" electrodes 402 serving as a ground plane. The distance between the centers of active electrodes (conductors) in each direction is a, and the distance between the vertical plane through the center of an active electrode and that through the center of a ground electrode is a/2. As well, the distance between the centers of common or ground electrodes is a. This configuration 500 may be used atop a cylindrical towed body 903 as shown in FIG. 9 to yield real time visualization of washover. For small towed bodies, typical values for a are approximately 5.0 cm (2") and for L are approximately 100 cm (40"). Further, a preferred embodiment of the present invention may be implemented in a simulator such that an expensive object of interest is simulated by an inexpensive model that mimics its shape, center of gravity, mass, orientation, etc. The model may be provided as a full-scale or, in the case of particularly large objects, a partial scale replica of the object with the configuration of the electrode array scaled accordingly.

Of course, the configuration 500 is "surface mated," e.g., flush-mounted in the case of the use of an external configuration of the array on an object upon which it is placed. That is, if it is placed on a cylinder, it takes the shape of the shell of the cylinder and does not lie in a flat plane. In the example of an externally mounted configuration, the individual electrodes may be any of various types of metal screws capable of being inserted flush with the outer surface of the outer shell of an object, and inserted with or without electrically-insulating gaskets depending on the composition of the shell (dielectric or conductor) and the instrumentation setup.

Figure 6:
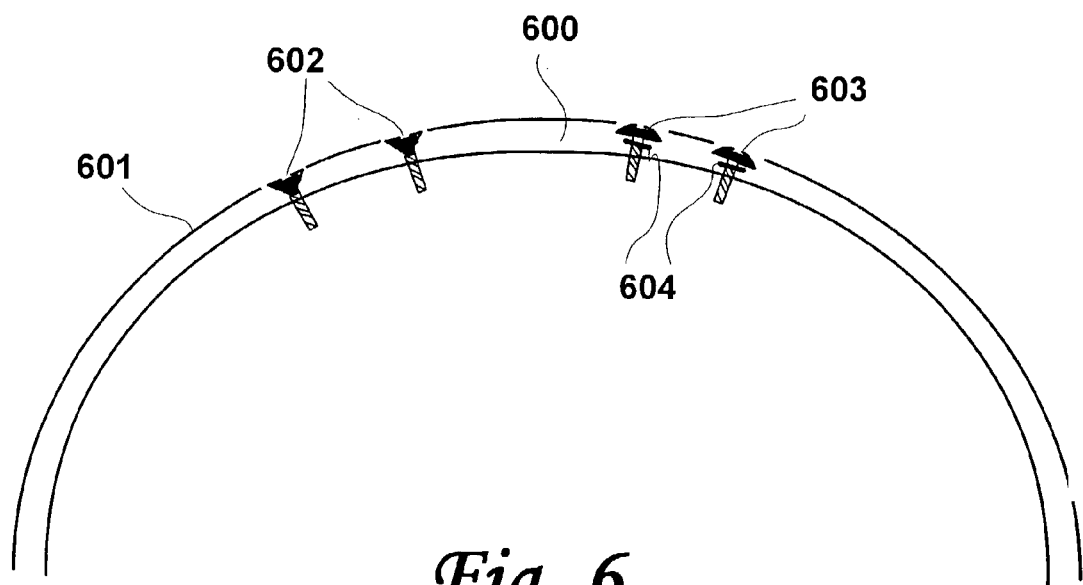
FIG. 6 depicts alternate methods of attaching electrodes to the shell of an object that may experience washover.

Refer to FIG. 6. For conductivity-dependent methods, the electrodes 602, 603, here shown as two different types of metal screws, must protrude through the shell 600 of the test object. For best hydrodynamic operation these electrodes 602, 603 should be flush with the surface 601 of the outer shell 600 of the object. Electrodes may be emplaced by countersinking holes through the shell 600 with the holes matching pre-specified sizes of machine screws 602 that are sealed via a suitable sealant, such as an RTV sealant, or by using gasketed roundhead screws 603 placed in sockets counter bored into the shell 600. The gaskets 604, or RTV sealant, seal the interior of the object from incursion of liquid at washover and may also be used to electrically isolate the electrodes from a conductive outer shell.

Figure 7:
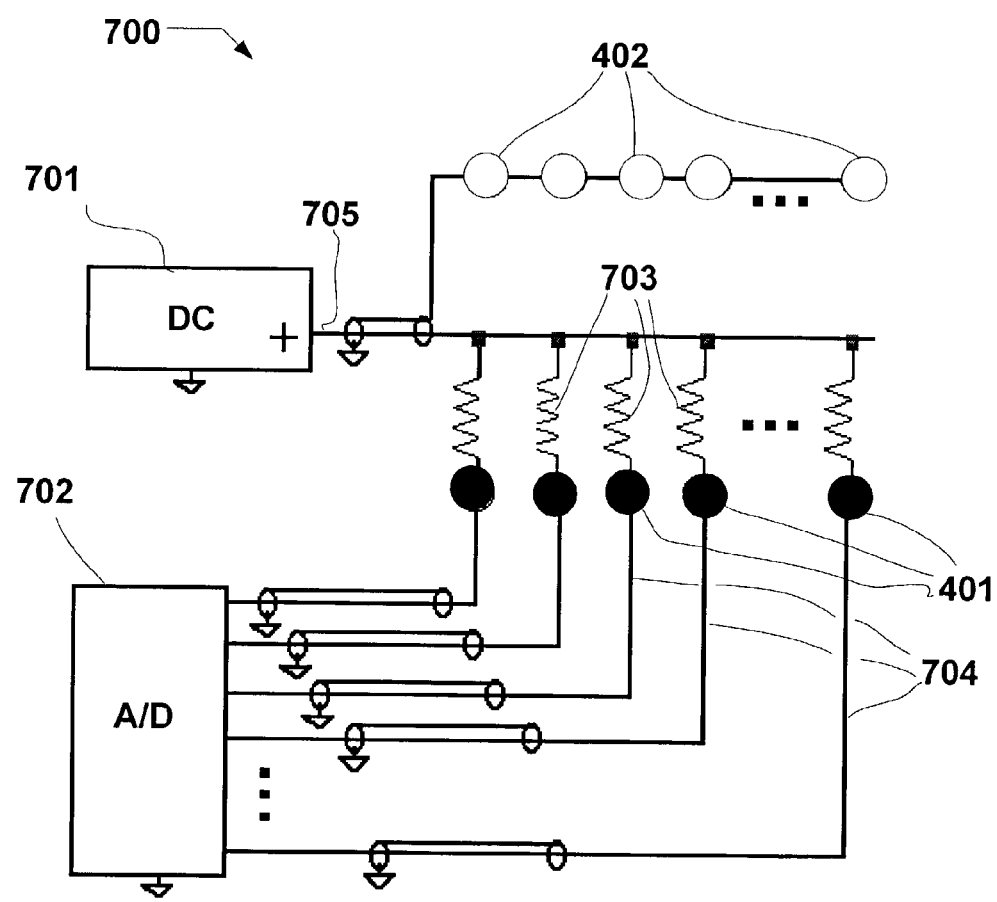
FIG. 7 is a schematic of the electrical portions of a preferred embodiment of the present invention.

Refer to FIGS. 7 and 9. Each pair of electrodes, i.e., at least one "common" 402 and one individual active sensor 401, is connected by a resistor 703 (typically 4.7–10 kΩ) at the active electrode. These "pull-up" resistors 703 provide sufficient impedance loading to the terminals to eliminate any random noise that may occur in the presence of an open-circuit impedance, e.g., no washover. Each individual active electrode 401 is connected, through the pull-up resistor, via a shielded coaxial cable (or circuit trace for a flexible board installation) 704 to the printed circuit card (or board) (multi-channel multiplexed data acquisition circuitry, incorporating an analog-to-digital converter) A/D 702. This card 702 is preferably controlled by a personal computer (PC) 901 and installed therein. Preferably, the PC 901 is located remotely, but may be located locally under some implementations. In one embodiment, the line 705 supplying the DC power to the electrode pairs 401, 402 is shielded similarly to the coaxial cables to improve the signal-to-noise ratio.

Figure 8:
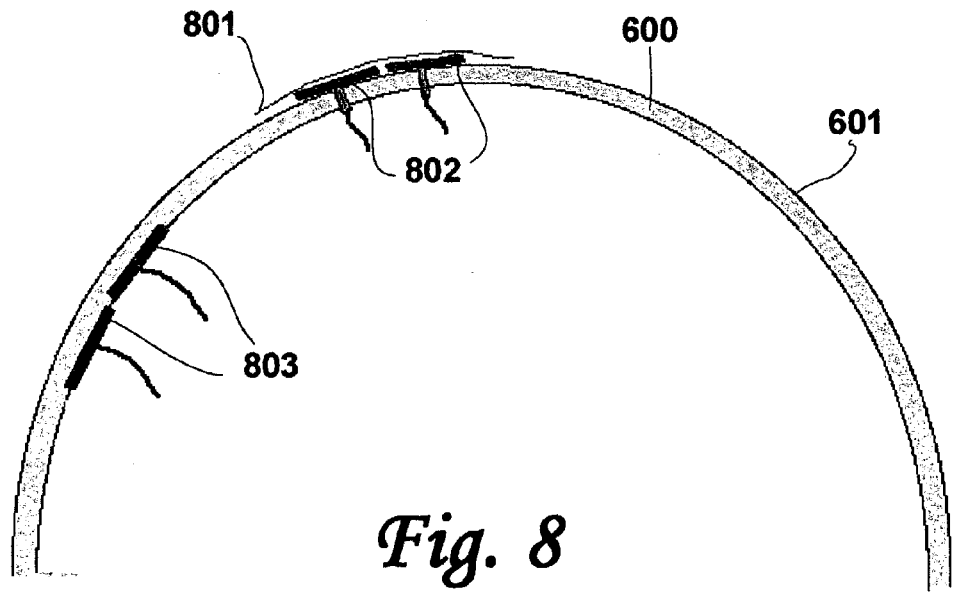
FIG. 8 depicts alternate methods of attaching capacitive electrodes to the shell of an object that may experience washover.

Refer to FIG. 8. For capacitive-dependent methods, the electrodes 803 may be mounted on the inside (dry side) of the shell 600 of the test object, assuming that the shell 600 of the object is a thin-walled dielectric, e.g., fiberglass, PLEXIGLAS®, or other plastic. Alternatively, these capacitive electrodes 802 may be surface mounted by coating them with a thin non-conductive dielectric coating 801 such as polyurethane.

Refer to FIGS. 7 and 9. Each electrode pair 401, 402 is connected to a shielded coaxial cable (or trace) 704, the active electrode 401 through a resistor 703. A long umbilical cable bundle 902 composed of multiple electrode-pair coaxial cables (or traces) 704 is fed out of a watertight port (not shown separately) on the instrumented object, such as a towed body 903. This bundle 902 is connected to a remote (preferably ship borne or land-based) multi-channel multiplexed data acquisition board or card (A/D) 702 that converts the analog measurements to digital signals. The board 702 is interfaced to a personal computer 901, preferably as an installed card therein. The electrode pair 401, 402 may be connected in either a balanced or unbalanced mode. In the balanced configuration, each member of the electrode pair 401, 402 is connected to a multiplexed, balanced input pair (not shown separately) on the board or card 702. In the unbalanced configuration, one electrode in each pair 401, 402 is wired to a common bus (not shown separately). This bus may provide grounding or power, depending on implementation. The other electrode lead of the pair 401, 402 is connected to a multiplexed input of the card 702. The choice of balanced or unbalanced configuration is dependent on data acquisition considerations that include both noise reduction and economy of implementation. The PC 901, preferably employing custom software, performs data acquisition, storage, processing, mapping and visualization functions.

EXAMPLE II

One of the prime applications for a preferred embodiment of the present invention is to obtain temporal and spatial washover data for verification of electromagnetic modeling of low-profile submarine antenna performance. This class of antenna rides very near the surface of the water and these antennas are therefore susceptible to significant wave interaction. The ability of a low-profile antenna to communicate with above surface elements during periods of submersion can be partially or completely inhibited depending on the depth, duration and period of submersion. Skin depth, $\delta_S$ (m), is defined as the depth at which a conductor's current is reduced to 0.368 of the surface value, equivalent to a power loss of 8.7 dB. Doubling the value of $\delta_S$ doubles the loss. Skin depth is frequency dependent, i.e., the higher the frequency, the shallower the skin depth. Skin depth can be defined mathematically as:

$$\delta_s = \sqrt{\frac{2}{\omega\mu\sigma}} = \sqrt{\frac{\rho}{\pi f \mu}} \quad (5)$$

where:
μ=permeability (For seawater, $\mu=\mu_0=4\pi \times 10^{-7}$ Henrys/m)
ρ=resistivity (Ω-m)
ω=radian frequency=2πf (Hz)
σ=conductivity (mho/m)=$\rho^{-1}$, (where mho [$\Omega^{-1}$]=Siemen [S])

Figure 10:
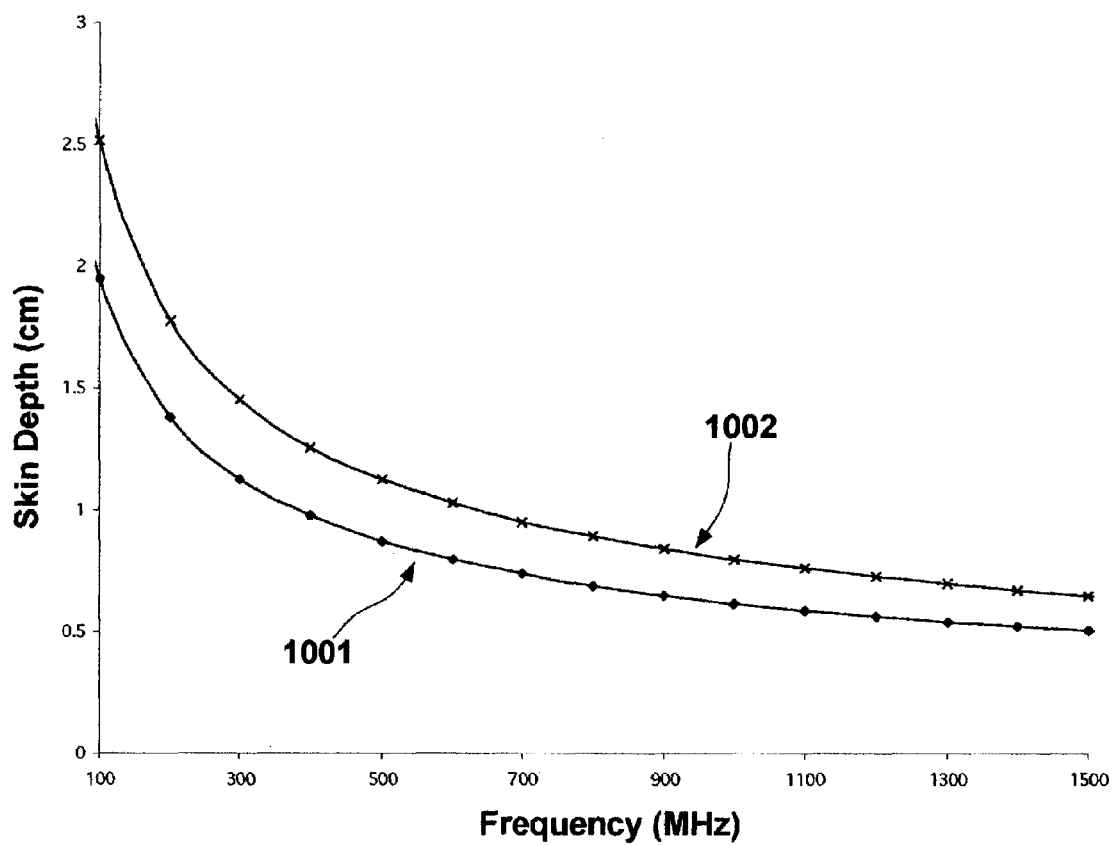
FIG. 10 depicts the relationship (for two values of conductivity) between skin depth and frequency for an antenna designed to float in seawater.

FIG. 10 illustrates the frequency dependency of skin depth for the range of resistivity typically expected in seawater, 0.15 Ω-cm at 1001 and 0.25 Ω-cm at 1002. As can be seen in the figure, across the VHF and UHF spectrum, skin depth is on the order of a few centimeters (0.5–0.75") or less and decreases with increasing frequency. For a frequency of 1000 MHz (1 GHz) the skin depth is approximately 0.75 cm (0.3"). Thus, at the preferred higher frequencies even relatively shallow washover has a profound effect on transmitted and received signal levels.

Refer to FIGS. 7 and 9. The system used to conduct tests of the present invention consists of several interconnected components: a sensor array 500 on the object 903 being tested, an umbilical tether 902 incorporating data and signal cables (traces) 704, 705 and a personal computer 901 for data acquisition, processing, storage and display.

The implementation for this test includes a sensor array 500 positioned along the axis of the test object 903 as previously described. The test object 903 was fitted with a counter-weighted keel (not shown separately) to ensure that the sensor array 500 remained at the topmost portion of the test object 903, a thin-walled fiberglass cylinder. The instrumented section of the test object 903 is 23 cm (9") in diameter and 1.0 m (39") long. The electrodes 401, 402 protrude through the shell 600 of the test object 903 to permit electrical contact with seawater washover 905.

Refer to FIG. 6. To ensure minimal interference with the hydrodynamic characteristics of the test object 903, these electrodes 401, 402 are flush-mounted with the surface 601 of the test body shell 600. The electrodes 401, 402 are stainless steel, O-ring gasketed machine screws inserted into countersunk holes through the test object 903 and fastened to an internal frame (not shown separately) and wiring harness (not shown separately).

Refer to FIG. 7. Each active (sensing) electrode 401 of the array 500 is connected by a 4.7 KΩ resistor 703 to the positive terminal of a DC source 701, thus providing sufficient impedance loading to the terminals to eliminate pickup of random noise that occurs if an open-circuit impedance were present. The test object 903 was fitted with a hydrodynamic nose (not shown separately).

Refer to FIG. 9. The tether and signal cable bundle 902 consisted of 63 individual 30 m lengths of RG-174 coaxial cable connected from the electrode array 500 to a remotely located personal computer 901 with a 64-channel analog-to-digital converter 702. The line 705 supplying the DC power to the electrode pairs 401, 402 is a shielded 30 m length of RG-58 for increased noise immunity. All 63 (21×3) electrode cables (traces) 704 and the power supply cable 705 were bundled in a plastic tube 902 extending from the personal computer 901 and terminating in a watertight fitting (not shown separately) where the cables (traces) 704, 705 passed into the sealed test object 903. The plastic tubing 902 also provided some buoyancy and mechanical strength to the umbilical cables (traces) 704, 705.

The personal computer 901 equipped with a 64-channel, 16-bit analog-to-digital converter 702 and programmed in LABVIEW® performed the data acquisition, processing, storage, mapping and visualization functions. The 63 active (sensing) electrodes 401 were sampled every 100 ms to enable fully capturing the dynamics of the washover wave action.

An initial operational test was performed by wiping a seawater-soaked sponge (not shown separately) along the sensor matrix 500 and observing the change in conductivity generated thereby. This test confirmed that all 63 active (sensing) electrodes 401 in the array 500 were properly connected and that the data acquisition, processing and display system 901 was operating properly.

Once fully integrated, the system was tested in a seawater wave tank (not shown separately). The water salinity was 15 parts per thousand, resulting in a conductivity of 20 mS/cm. The test tank measured 10 m (33') by 30 m (100') and was 1.5 m (5') deep. At one end of the tank was a motor-operated paddle system (not shown separately) that produced waves with a maximum amplitude of approximately 30 cm (12") at a period of one second.

The test object 903 was placed in the seawater wave tank, tethered fore and aft to orient it relative to the wave front, and subjected to the wave action. Several hours of continuous washover data were observed in real-time within a range of wave conditions. Several minutes of continuous data were recorded in an ASCII spreadsheet format.

Figure 11:
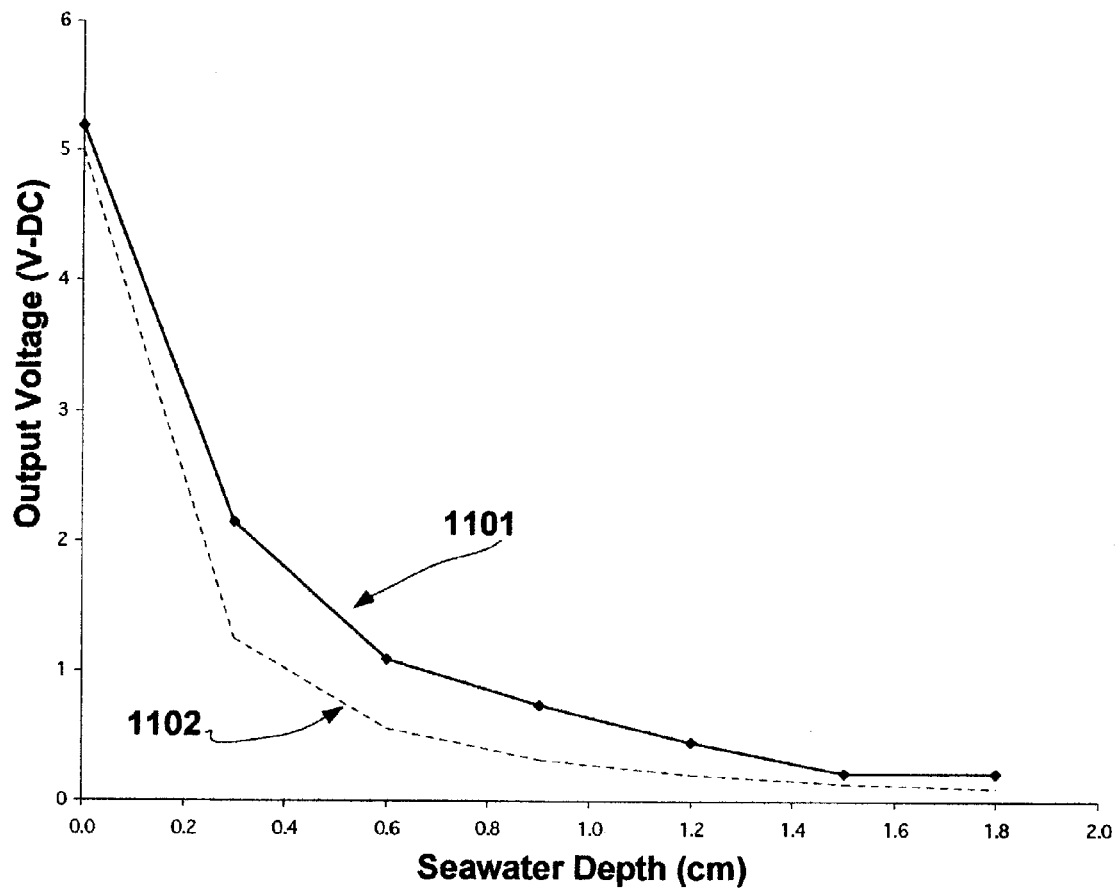
FIG. 11 depicts the relationship between measured DC-voltage and seawater depth, i.e., a calibration curve, as compared to the theoretical $1/r^2$ falloff relationship.
Figure 14:
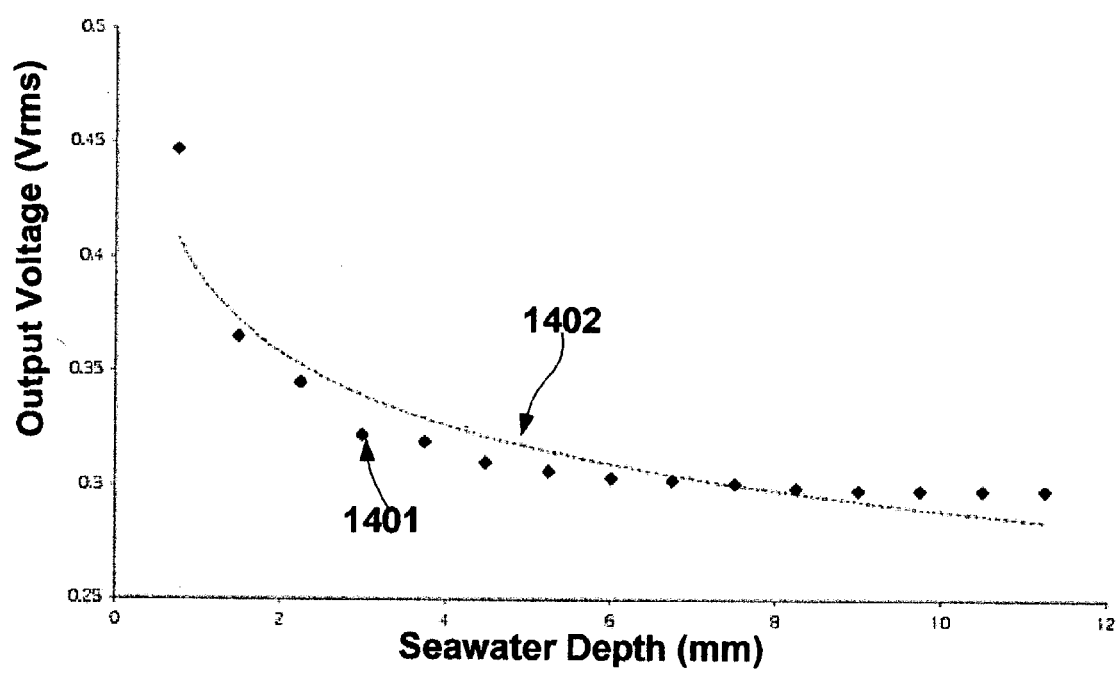
FIG. 14 depicts the relationship between measured AC-voltage and seawater depth, i.e., a calibration curve, as compared to the theoretical $1/r^2$ falloff relationship.

Refer to FIG. 14. A calibration was performed with a duplicate of the tested array 500. The electrodes 401, 402 of the array 500 were built into the bottom of a plastic cup (not shown separately). Constant depth increments of seawater were added to the cup and a DC source (not shown separately) impressed on the active electrodes 401. The calibration curve 1401 generated therefrom compares favorably to the theoretical $1/r^2$ falloff of a reference curve 1402, as shown in FIG. 14. Compare to the calibration curve 1101 of FIG. 11 and the reference curve 1102 in which a DC voltage source was used.

Figure 12:
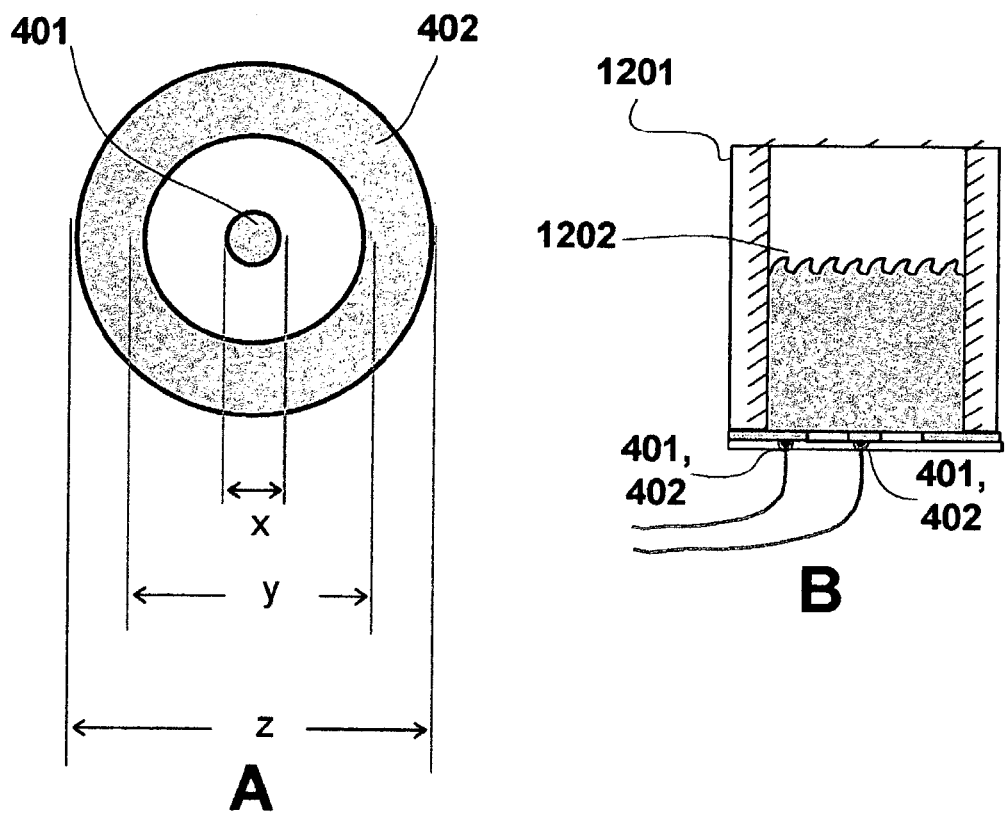
FIG. 12A shows an electrode configuration for a test setup for one experiment done in conjunction with developing the present invention.
FIG. 12B depicts a second test setup for calibrating a configuration of the present invention to the theoretical $1/r^2$ falloff relationship.
Figure 13:
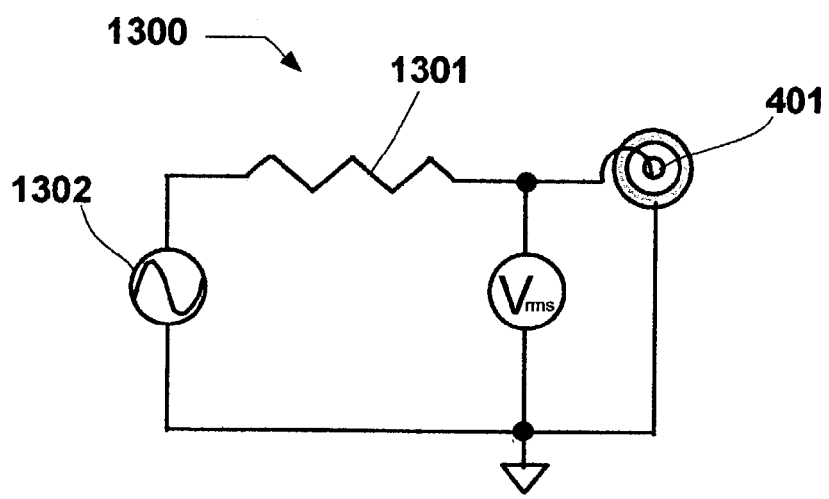
FIG. 13 depicts a circuit used to test the electrode configuration shown in FIG. 12A.

Refer to FIGS. 12 and 13. A second calibration experiment was performed in a similar manner using a cup 1201 filled with seawater 1202 as shown in FIG. 12B, but with an electrode configuration consisting of a "washer-shaped" solid ground plane 402 of inside diameter y and outside diameter z surrounding a single electrode 401 of diameter x as shown in FIG. 12A. The test circuit 1300 is shown in FIG. 13. An AC source 1302, impressed upon a suitably sized resistor 1301, was used in this experiment to limit the effects of galvanic-based erosion of the sensor electrodes 401, 402. Since a DC source 701 was used in the preliminary experiments, some minor erosion due to galvanic action was expected but not observed. Since applications of preferred embodiment of the present invention are for short time periods, i.e., sensor current applied for an hour or less, this erosion is of little concern. For longer duration experiments, the effects of erosion may be substantial and may adversely affect the contact impedance between the electrode and seawater. Thus, a solution for longer test periods is to power the sensor with an AC current. The alternating polarity of the AC current should significantly lessen erosion. However, an AC-powered implementation is more complex than a DC-powered one, requiring full-wave rectification and filtering prior to digitization of the data signal. For acceptable temporal resolution of wave action, the AC current should be at a frequency of an order or two of magnitude greater than that of the wave action. Additionally, the time constant of low-pass filtering applied to the pre-digitization full-wave rectification should be set appropriately. This is known to one skilled in this art.

Figure 15:
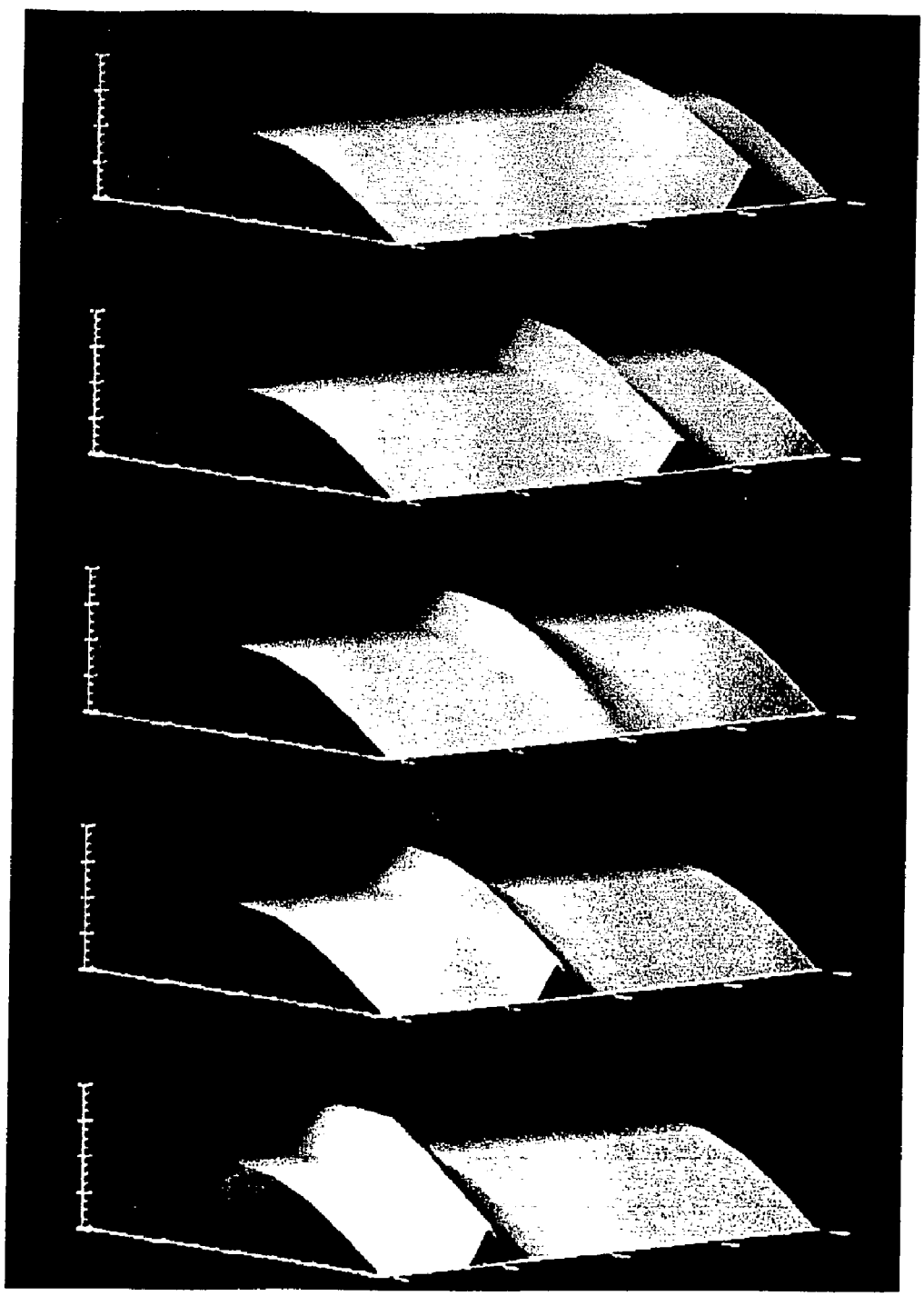
FIG. 15 is a sequential conformally mapped representation of the response of a preferred embodiment of the present invention to being wiped with a sponge soaked in seawater.

FIG. 15 illustrates an IDL®-processed sequence of the results of passing a seawater-moistened sponge across the electrode array 500. The sponge was passed from the viewer's right to left and the result is documented sequentially from top to bottom in FIG. 15. The sharp contrast between the low conductivity of dry electrode elements compared with the band of electrode elements moistened by the sponge is evident in the "barrel ribs."

Figure 16:
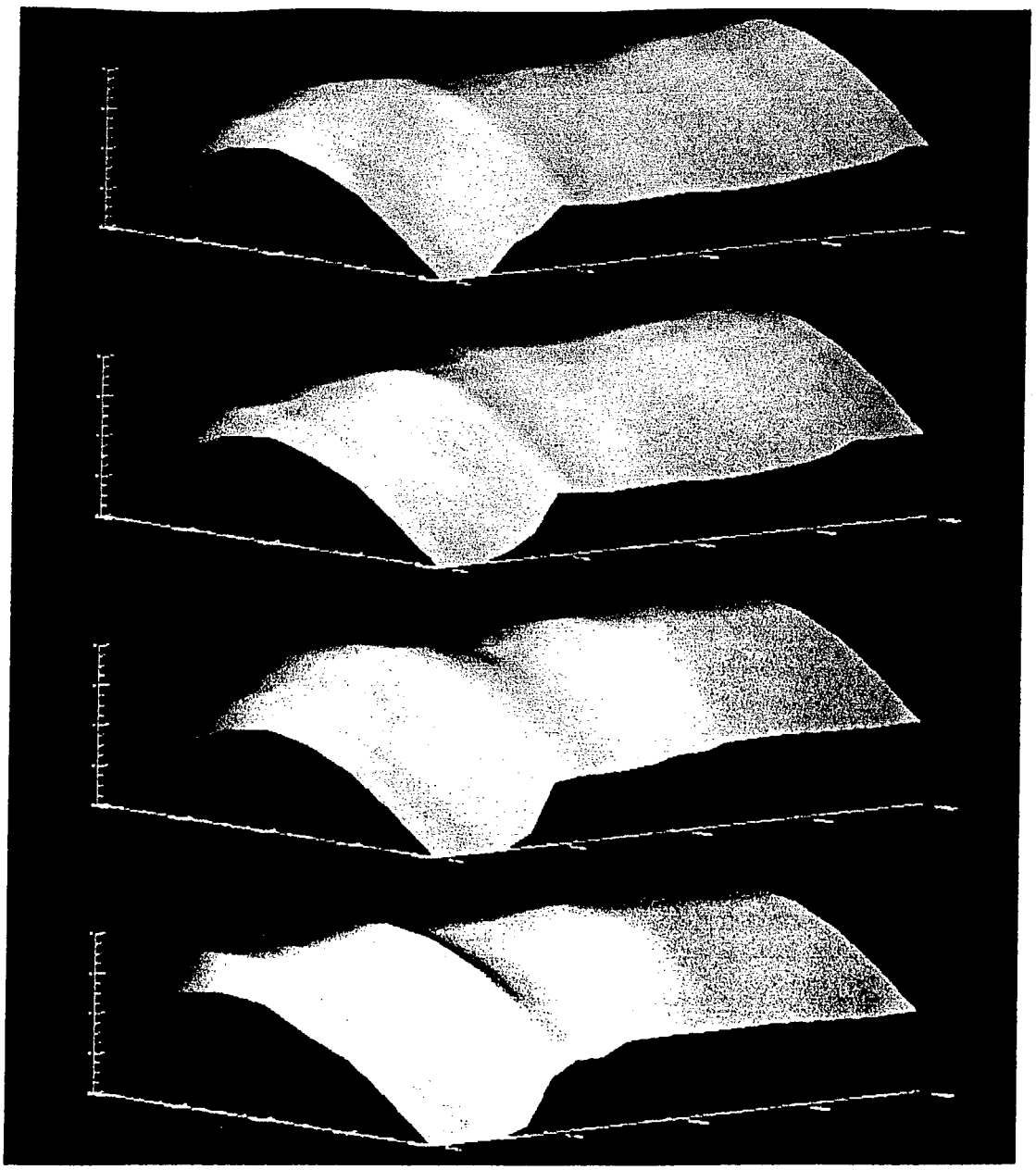
FIG. 16 is a sequential conformally mapped representation of the response of a preferred embodiment of the present invention in actual use during a test within a tank filled with seawater.

Refer to FIG. 16. A data file obtained from one experiment was post-processed using IDL®. A complete sequence of washover events was spatially interpolated and conformally plotted, giving a 3-dimensional visualization of the washover wave action. FIG. 16 illustrates several frames of that sequence (top to bottom). This data set was processed and converted to digital animations for replay and analysis.

EXAMPLE III

In laboratory scale mockups and certain unique test setups, one may tolerate a requirement to build an electrode array into each individual object to be tested. While this technique provides an excellent means of acquiring data, such as washover data, the precision machining, fabricating, and hand-wiring of the object with the sensor array is labor intensive and expensive. Each tested object must be fabricated individually in this manner. For example, existing towed bodies must be modified irrevocably to perform washover testing. In this process of modification, significant changes in buoyancy and center of buoyancy may occur, thus adversely affecting a device's hydrodynamic performance. Multiple holes are drilled into a formerly watertight body and special corrosion-resistant gasketed screws are inserted through the body and mated with a wiring harness internal to the towed body. The resulting physical configuration may yield skewed test results since implementing an "integrated" sensor array changes the established density and moment of inertia of the object, among other characteristics.

Figure 17:
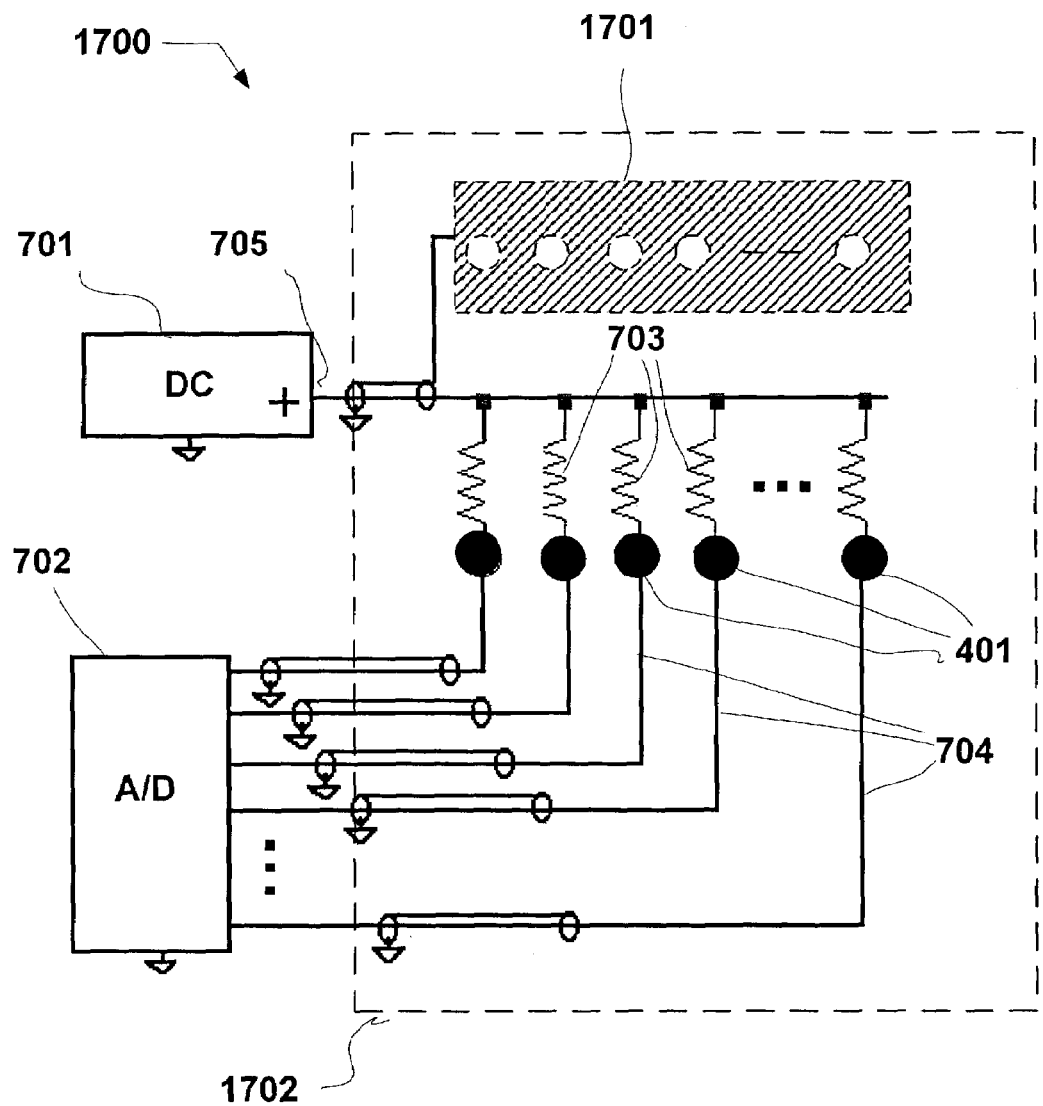
FIG. 17 depicts an alternative schematic to FIG. 7 for an embodiment used in non-destructive testing (NDT) of an object, i.e., no physical alteration is made to the object.
Figure 18:
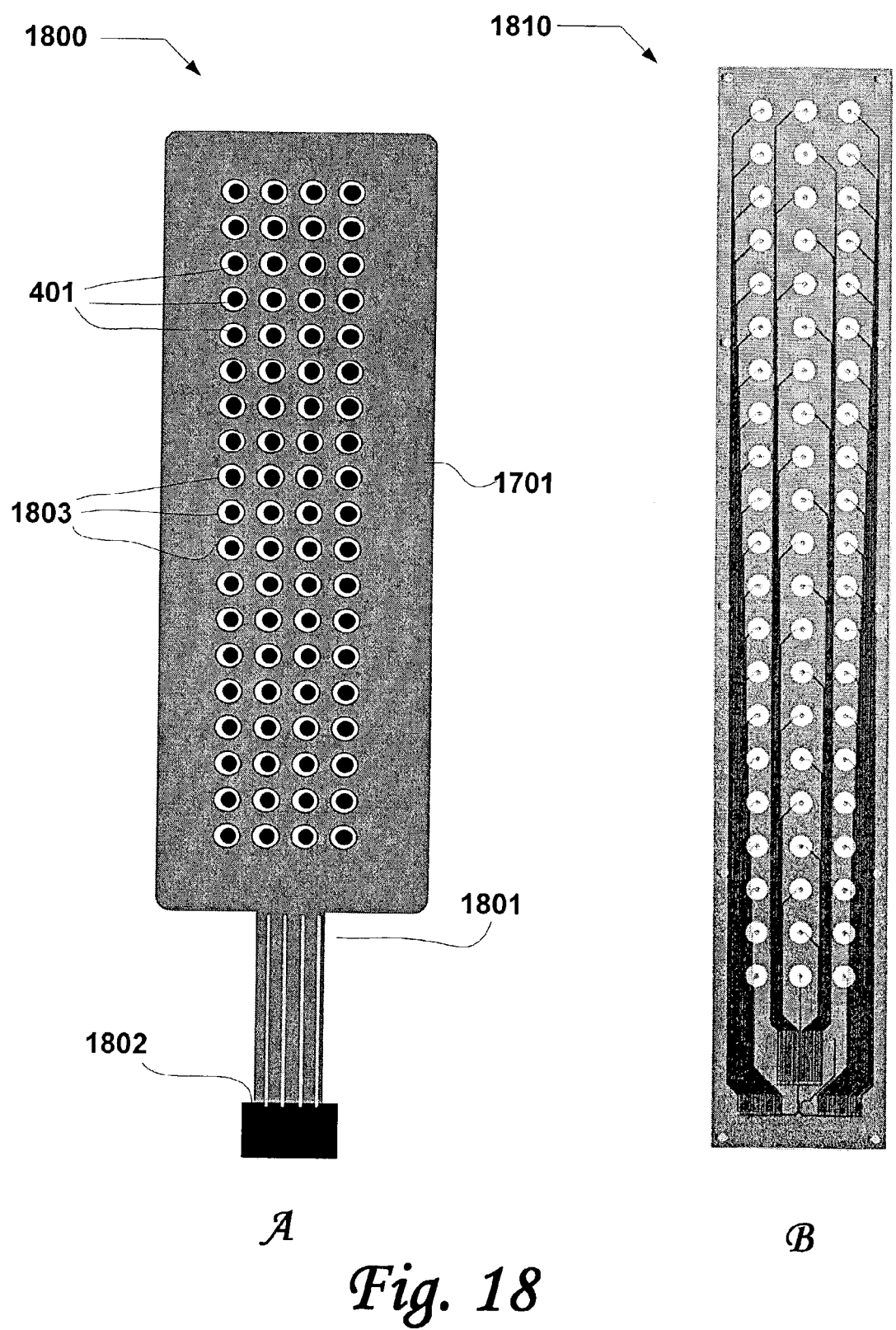
FIG. 18A shows a top view of an embodiment as used with the schematic of FIG. 17.
FIG. 18B shows a layout of sensors that may be used in the embodiment of FIG. 18A.

Refer to FIGS. 17 and 18. This process may be simplified in an arrangement 1700 by using a conformal, flexible printed circuit sensor array 1702 that may be affixed, using a temporary waterproof adhesive, to the external surface of an object, even those having an irregular contour. The conformal array 1702 is further simplified by having the ground plane 1701 surround the individual sensors 401, with an insulation ring 1803 (as shown in FIG. 18) around each sensor 401. By employing an appropriate temporary adhesive, the embodiment 1800 may be removed after testing, enabling it to be reused on other objects without modification of the object or the array 1702.

This embodiment 1800 of the sensor array 1702, as also depicted in top view on a flexible circuit board 1810, couples via a flat wire bundle 1801 to a commercially available tow cable 902 with a commercially available off-the-shelf (COTS) watertight electrical connector 1802, thus facilitating re-use of the array 1702 with other test objects. Further, only one multi-conductor instrumentation cable inserted in the tow cable 902 with appropriate watertight connector 1802 is required.

Figure 20:
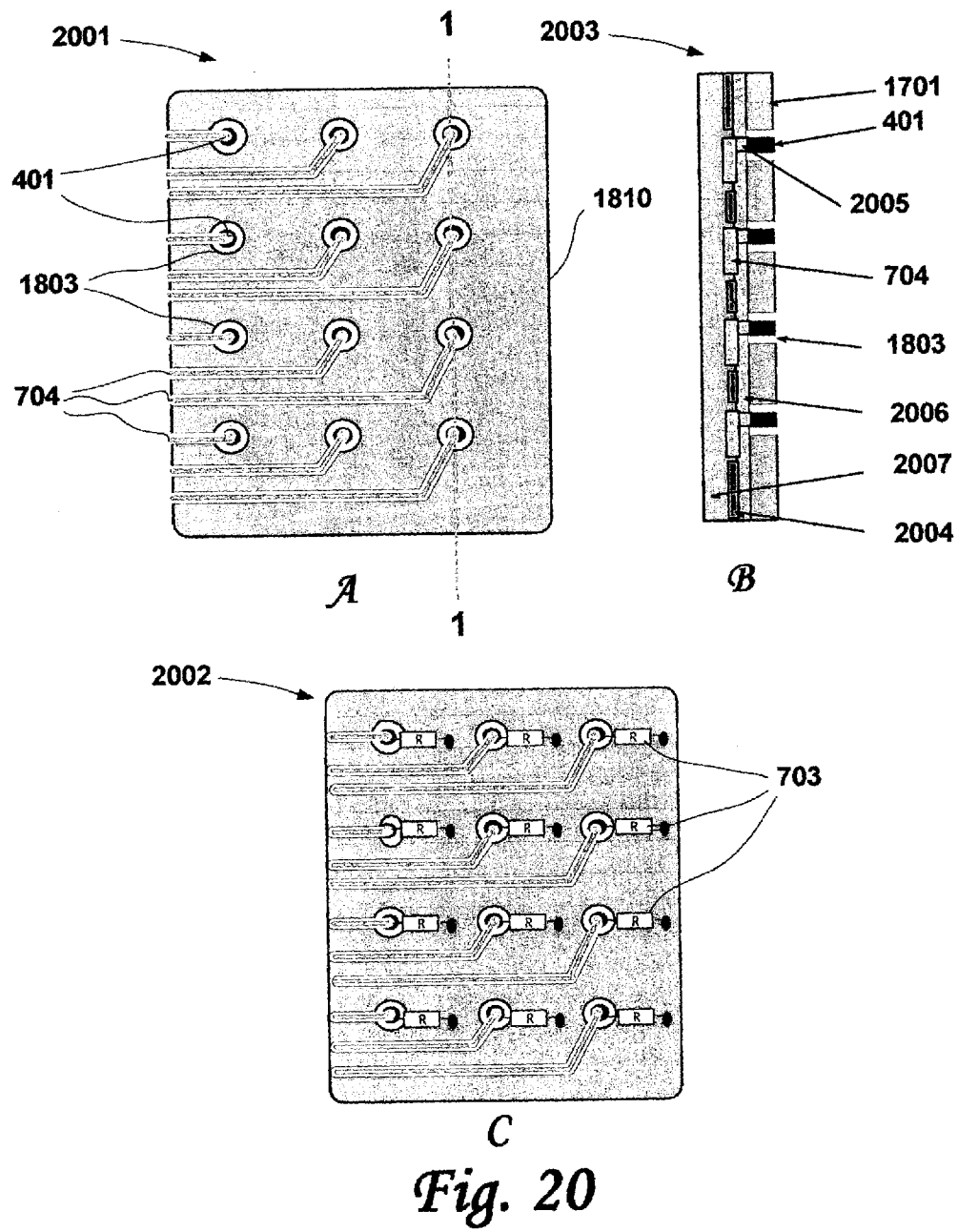
FIG. 20A shows a bottom view of a layout of the sensors shown in a top view in FIG. 18A.
FIG. 20B shows an edge view of the sensor layout through cut 1—1 of FIG. 20A.
FIG. 20C shows a preferred configuration of the pull-up resistors depicted in the schematic of FIGS. 7 and 17 along the bottom side of the array shown in FIG. 18.

Refer to FIG. 20. FIG. 20A depicts a bottom view (without the insulating laminate) of a preferred embodiment 2001 of the array 1702 as fabricated on a double-sided, flexible printed circuit board 1810, a sample of which is seen in a top view in FIG. 18B.

Refer specifically to FIG. 20B, an edge view 2003 of FIG. 20A taken through 1—1. The array 1702 consists of a number of individual electrodes (sensors) 401 surrounded, and electrically insulated by insulating rings 1803 from an electrical ground plane 1701. Thus, the electrode points 401 are isolated from the surrounding ground plane 1701, and both the common conductive plane 2004 (here established with a positive voltage) and electrodes 401 are electrically exposed for contact with any intermittent exposure to material, such as seawater washover 905. Each individual electrode 401 is connected through the double-sided, flexible, printed circuit board 1810 by vias 2005 to individual conductive printed circuit traces 704. These conductive traces 704, insulated from the common conductive plane 2004 by an insulating substrate 2006 connect each electrode 401 to a pin (not shown separately) on a watertight electronic multi-pin jack (pins not shown separately but part of the COTS connector 1802). An insulating laminate 2007 provides the backing to which a waterproof adhesive may be applied.

On the back side (as shown in FIG. 20A and in an alternative configuration in FIG. 20C with the insulating laminate "removed" for illustration) of the flexible circuit board 1810, each trace 704 is surrounded, but isolated from a second conductive plane 2004 that is connected 705 to the positive terminal of a DC power supply 701. Between each of the individual traces 704 and the surrounding positive voltage conductive plane 2004, a pull-up resistor 703, nominally 10 KΩ, is connected to bias positively the input terminal of the associated analog-to-digital (A/D) converter 702. Using surface mount devices to maintain a low profile, these pull-up resistors 703 may be soldered directly onto the back side 2002 of the flexible circuit board 1810 as shown in FIG. 20C. Alternatively these pull-up resistors 703 may be mounted in a housing nearby (not shown separately) or provided integral to the watertight connector 1802.

The bottom side 2001, 2002 of this circuit board 1810 is coated in a waterproof laminate (or coating) 2007 (shown only in the edge view of FIG. 20B) to facilitate conformally affixing it to any shape. By the application of a suitable "temporary" or "removable" waterproof adhesive, the conformal element 1800 can be easily removed and reused in subsequent tests.

Figure 19:
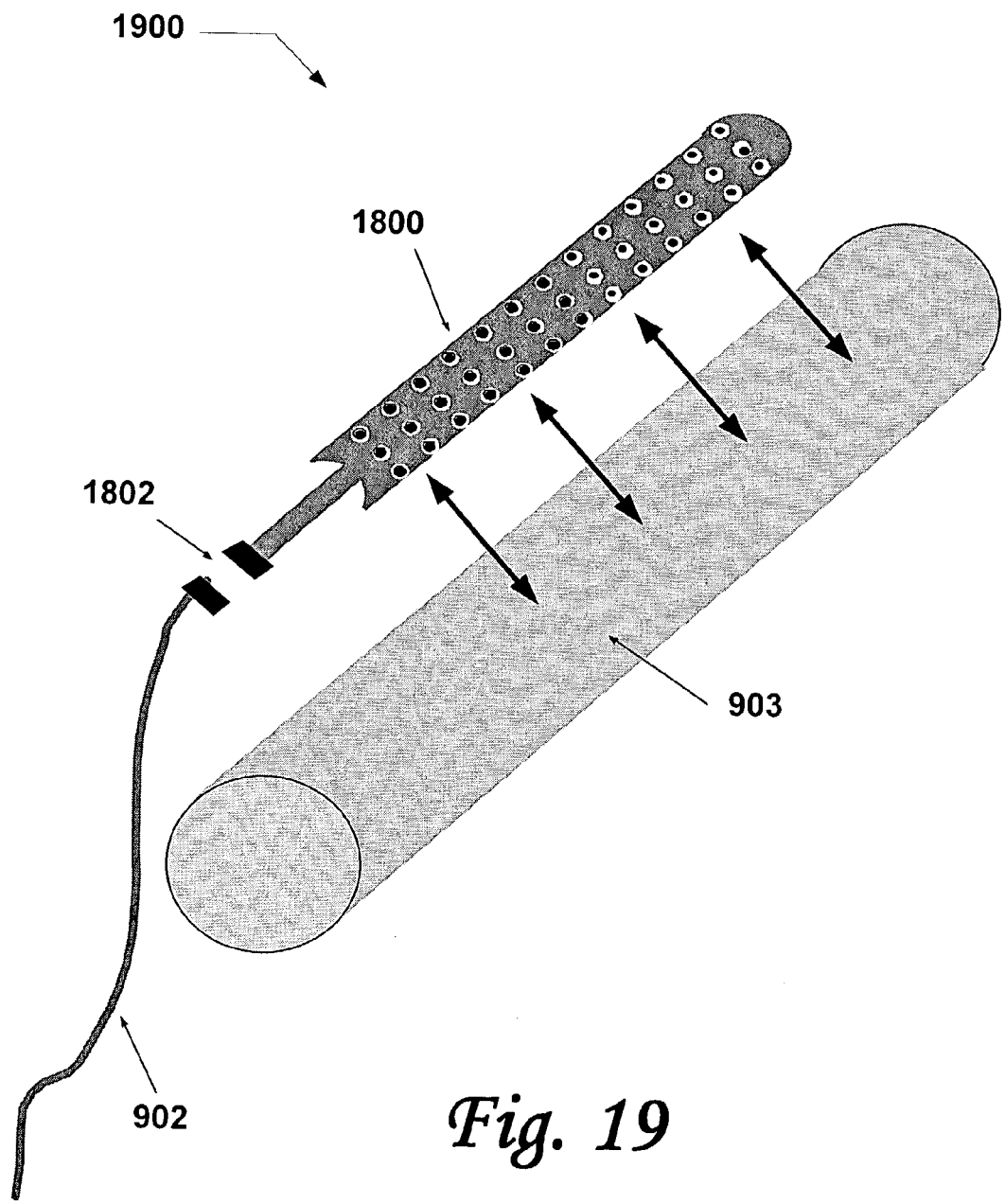
FIG. 19 shows how the embodiment of FIGS. 17 and 18 may be applied to a cylindrically shaped object.
Figure 21:
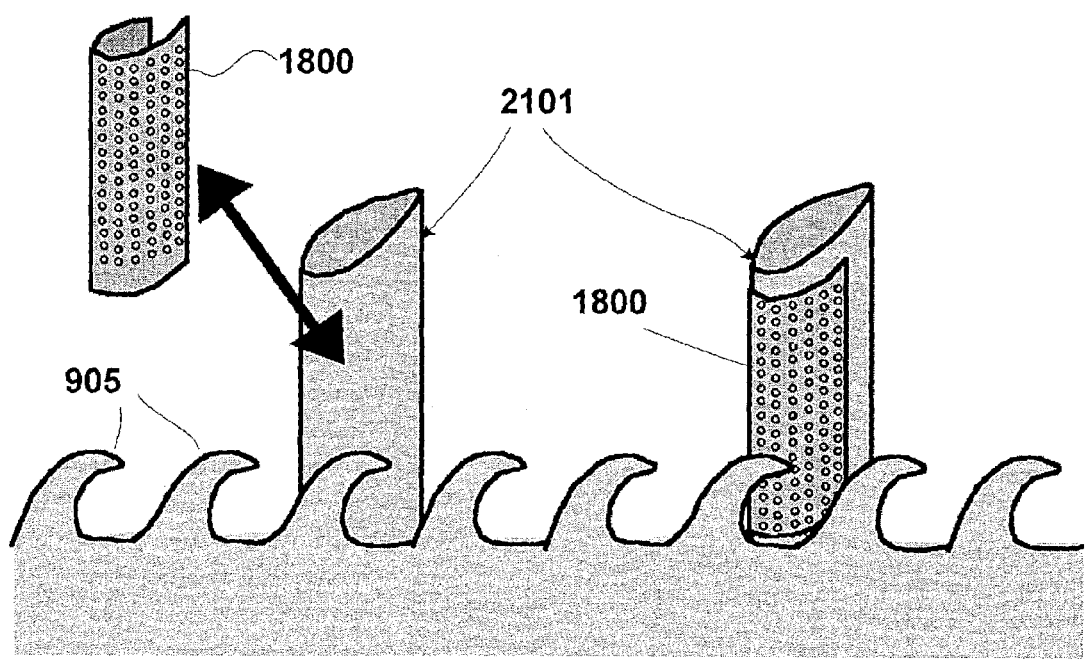
FIG. 21 depicts an embodiment as may be used in a vertical orientation on submarine masts.

Refer to FIGS. 19 and 21. In application, the conformal, flexible, sensor system 1800 may be affixed by an adhesive to an actual functional object 903 as depicted at 1900. Further, as shown in FIG. 21, the sensor system 1800 may be applied to vertical surfaces as shown with antenna masts 2101 that may be employed on submarines.

Although DC current is the preferred implementation in non-laboratory scenarios, AC current, at a wide range of frequencies, may also be used. In summary, the advantages of a flexible, conformable, "re-usable" embodiment include:
  ready implementation of a simple, low cost technique;
  no alteration to functional equipment to be tested;
  reusable;
  readily conformable to irregular contours;
  reduced cost of testing, i.e., no specialized re-configuration of object under test;
  inherent accuracy of measurement of the object as it will be configured for actual use; and
  reduced time to implement testing and produce objective comparable results.

While the invention has been described in terms of its preferred embodiments, one skilled in the art will recognize that the invention may be practiced with modifications within the spirit and scope of the appended claims. For example, although the system is described in specific examples for mapping, visualizing, or imaging washover, it may operate on any surface and in conditions that one would wish to map occurrences on a surface, such as drifting snow, drifting sand or silt, sediment, etc., both in a practical implementation and in a scaled experimental testing facility such as a wind tunnel, wave tank, etc. It may be suitable for other applications such as determining operating conditions in a manufacturing plant, e.g., calibrating the process establishing the thickness and uniformity of a polishing liquid use on a silicon wafer for purposes of optimizing polishing, quality sampling the process for layering a coating of chocolate on a confection, etc. Further, monitoring 3-D depth of a molten wax, oil or liquid plastic in a wave-coating tank may be another possibility.

Thus, it is intended that all matter contained in the foregoing description or shown in the accompanying drawings shall be interpreted as illustrative rather than limiting, and the invention should be defined only in accordance with the following claims and their equivalents.

We claim:

1. A system for detecting, measuring and recording fluid washover of an object at multiple locations simultaneously, to include displaying a representation of said fluid washover in real time, comprising:
    an array of electrically-isolated electrode pairs affixed to be conformal with at least one side of an external surface of said object,
wherein an electric potential is maintained between the electrodes of each said electrode pair during operation of said system, and
wherein said configuration of said array is chosen to provide a pre-specified level of detail of said washover;
    at least one electrical connection in operable communication with each said electrode of said electrode pairs; and
    a data collection, processing, recording and display sub-system in operable communication with said at least one electrical connection,
wherein said data collection, processing, recording and display sub-system collects data representing the time of sampling, the location of said sampling, and said sampling of at least one electrical characteristic of any fluid accumulating between said electrode pairs, processing said data for real time display as well as recording selected said data for future use.

2. The system of claim 1 in which said at least one electrical characteristic is selected from the group consisting of: resistance, complex impedance, inductance, and capacitance.

3. The system of claim 1 in which one said electrode in each said pair is electrically activated and the other said electrode is held at an electrical potential common to all like said electrodes in said array of electrode pairs.

4. The system of claim 3 in which said electrode held at an electrical potential common to all like said electrodes is incorporated as a single ground plane common to all electrode pairs,
wherein each electrode pair comprises said common ground plane and said electrically activated electrode.

5. The system of claim 1 in which said array comprises at least one conformable printed circuit that is removably affixed to said external surface.

6. The system of claim 1 in which said array is flush-mounted to the external side of said external surface.

7. The system of claim 6 in which said electrodes are any of various types of machine screws inserted in counter-bored holes in said external surface.

8. The system of claim 1 in which said electrode pairs are capacitive devices affixed to the internal side of said external surface.

9. The system of claim 1 in which said electrode pairs are capacitive devices covered with a thin coating of a dielectric.

10. The system of claim 9 in which said dielectric is a polyurethane.

11. The system of claim 1 in which said at least one electrical connection is a wire incorporating an electrically insulating cover,
wherein each said wire is bundled with like said wires to facilitate a durable connection to said sub-assembly.

12. The system of claim 11 in which said wire is shielded coax.

13. The system of claim 11 in which said at least one electrical connection provided to each said active electrode also comprises at least one pull-up resistor.

14. The system of claim 1 in which said data collection, processing, recording and display sub-system comprises:
    at least one multi-channel multiplexed data acquisition printed circuit board incorporating at least one analog-to-digital converter;
    at least one personal computer, incorporating a display, in operable communication with said at least one multi-channel multiplexed data acquisition printed circuit board; and
    software loadable on said at least one personal computer for processing said data.

15. The system of claim 1 in which said fluid is a liquid and said object floats in said liquid such that at least part of said object is not in communication with said liquid when said liquid is not acted on by forces external thereto.

16. The system of claim 15 in which said liquid is seawater and said object is a towed body.

17. A method for detecting, measuring and recording fluid washover of an object at multiple locations simultaneously, to include displaying a representation of said fluid washover in real time, comprising:
    providing an array of electrically-isolated electrode pairs affixed to be conformal with at least one external surface of said object,
    maintaining an electric potential between the electrodes of each said electrode pair, and
    collecting as data samples of at least one electrical characteristic of said fluid together with the time and location of each said collected samples, said fluid accumulating that accumulates between each electrode pair during selected events of said washover;
    processing said collected data;
    recording selected said processed data; and
    displaying selected said processed data,
wherein said data collecting, processing, recording and displaying of said at least one electrical characteristic as correlated to a location and time enables visualization of said washover in a real time display as well as the recording thereof for future use.

18. The method of claim 17 selecting said at least one electrical characteristic from the group consisting of: resistance, complex impedance, inductance, and capacitance.

19. The method of claim 17 electrically activating one said electrode in each said pair and holding the other said electrode at an electrical potential common to all like said electrodes in said array of electrode pairs.

20. The method of claim 19 incorporating said electrode held at an electrical potential common to all like said electrodes as a single ground plane common to all electrode pairs, wherein each electrode pair comprises said common ground plane and said electrically activated electrode.

21. The method of claim 17 said fluid comprising a liquid and said object floating in said liquid such that at least part of said object is not in communication with said liquid when said liquid is not acted on by forces external thereto.

22. The method of claim 21 said liquid comprising seawater and said object being a towed body.

23. The method of claim 17 said array comprising at least one conformable printed circuit that is removably affixed to said external surface.

24. A simulator for detecting, measuring and recording fluid washover of an object at multiple locations simultaneously, to include displaying a representation of said fluid washover in real time, comprising:
 a model of said object;
 an array of electrically-isolated electrode pairs affixed to be conformal with at least one external surface of said mode,
wherein an electric potential is maintained between the electrodes of said electrode pair during operation of said simulator, and
wherein said configuration of said array is chosen to provide a pre-specified level of detail of said washover;
 at least one electrical connection in operable comniunication with each said electrode of said electrode pairs; and
 a data collection, processing, recording and display sub-system in operable communication with said at least one electrical connections,
wherein said data collection, processing, recording and display sub-system collects data representing the sampling of at least one electrical characteristic of any fluid accumulating between said electrode pairs and the time and location of said sampling, processes said data for real time display and records selected said data for future use.

25. A system for detecting, measuring and recording interaction of an object with its environment at multiple locations simultaneously, to include displaying a representation of said interaction in real time, comprising:
 an array of electrically isolated electrode pairs affixed to be conformal with at least one external surface of said object,
wherein an electric potential is maintained between the electrodes of each said electrode pair during operation of said system, and
wherein said configuration of said array is chosen to provide a pre-specified level of detail of said interaction;
 at least one electrical connection in operable communication with each said electrode of said electrode pairs; and
 a data collection, processing, recording and display sub-system in operable communication with said at least one electrical connections,
wherein said data collection, processing, recording and display sub-system collects data representing the sampling of at least one electrical characteristic of any material accumulating between said electrode pairs and the time and location of said sampling, processes said data for real time display and records selected said data for future use.

26. The system of claim 25 in which said at least one electrical characteristic is selected from the group consisting of: resistance, complex impedance, inductance, and capacitance.

27. The system of claim 25 in which one said electrode in each said pair is electrically activated and the other said electrode is held at an electrical potential common to all like said electrodes in said array of electrode pairs.

28. The system of claim 27 in which said electrode held at an electrical potential common to all like said electrodes is incorporated as a single ground plane common to all electrode pairs, wherein each electrode pair comprises said common ground plane and said electrically activated electrode.

29. The system of claim 25 in which said array is flush-mounted to the external side of said external surface.

30. The system of claim 29 in which said electrodes are any of various types of machine screws inserted in counter-bored holes in said external surface.

31. The system of claim 30 in which said array comprises at least one conformable printed circuit that is removably affixed to said external surface.

32. The system of claim 25 in which said electrode pairs are capacitive devices affixed to the internal side of said external surface.

33. The system of claim 25 in which said electrode pairs are capacitive devices covered with a thin coating of a dielectric.

34. The system of claim 33 in which said dielectric is a polyurethane.

35. The system of claim 25 in which said at least one electrical connection is a wire incorporating an electrically insulating cover,
wherein each said wire is bundled with like said wires to facilitate a durable connection to said sub-assembly.

36. The system of claim 35 in which said wire is shielded coax.

37. The system of claim 35 in which said at least one electrical connection provided to each said active electrode also comprises at least one pull-up resistor.

38. The system of claim 25 in which said data collection, processing, recording and display sub-system comprises:
 at least one multi-channel multiplexed data acquisition printed circuit board incorporating at least one analog-to-digital converter;
 at least one personal computer, incorporating a display, in operable communication with said at least one multi-channel multiplexed data acquisition printed circuit board; and
 software loadable on said at least one personal computer for processing said data.

39. A method for detecting, measuring and recording interaction of an object with its environment at multiple locations simultaneously, to include displaying a representation of said interaction in real time, comprising:
 providing an array of electrically isolated electrode pairs affixed to be conformal with at least one external surface of said object;
 maintaining an electric potential between the electrodes of each said electrode pair;
 collecting as data sampling of at least one electrical characteristic of material that accumulates between each electrode pair during selected events of said washover and the time and location of said sampling;
 processing said collected data,
 recording selected said processed data, and
 displaying selected said processed data, wherein said data collecting, processing, recording and displaying of said at least one electrical characteristic as correlated to time and location enables visualization of said interaction in a real time display as well as the recording thereof for future use.

40. The method of claim 39 selecting said at least one electrical characteristic from the group consisting of: resistance, complex impedance, inductance, and capacitance.

41. The method of claim 39 electrically activating one said electrode in each said pair and holding the other said electrode at an electrical potential common to all like said electrodes in said array of electrode pairs.

42. The method of claim 39 incorporating said electrode held at an electrical potential common to all like said electrodes as a single ground plane common to all electrode pairs,
wherein each electrode pair comprises said common ground plane and said electrically activated electrode.

43. The method of claim 39 said array comprising at least one conformable printed circuit that is removably affixed to said external surface.

44. A simulator for detecting, measuring and recording interaction of an object with its environment at multiple locations simultaneously, to include displaying a representation of said interaction in real time, comprising:

a model of said object;

an array of electrically isolated electrode pairs affixed to be conformal with at least one external surface of said model, wherein an electric potential is maintained between the electrodes of said electrode pair during operation of said simulator, and wherein said configuration of said array is chosen to provide a pre-specified level of detail of said interaction;

at least one electrical connection in operable communication with each said electrode of said electrode pairs; and a data collection, processing, recording and display sub-system in operable communication with said at least one electrical connections, wherein said data collection, processing, recording and display sub-system collects data represents the sampling of at least one electrical characteristic of any material accumulating between said electrode pairs and the time and location of said sampling, processes said data for real time display and records selected said data for future use.

* * * * *